(12) United States Patent
Wang et al.

(10) Patent No.: US 7,838,668 B2
(45) Date of Patent: Nov. 23, 2010

(54) METHOD FOR CRYSTALLIZING SUCRALOSE

(75) Inventors: Fei Wang, Nanjing (CN); Haibing He, Nanjing (CN); Yongzhu Yu, Nanjing (CN); Zhisong Fan, Nanjing (CN); Xin Yang, Nanjing (CN)

(73) Assignee: JK Sucralose Inc., Yancheng, Jiangsu Province (CN)

( * ) Notice: Subject to any disclaimer, the term of this patent is extended or adjusted under 35 U.S.C. 154(b) by 856 days.

(21) Appl. No.: 11/741,269

(22) Filed: Apr. 27, 2007

(65) Prior Publication Data

US 2008/0161552 A1     Jul. 3, 2008

(30) Foreign Application Priority Data

Dec. 27, 2006     (CN)     ........................ 2006 1 0156768

(51) Int. Cl.
    *C07H 1/06*     (2006.01)
    *C07H 1/08*     (2006.01)

(52) U.S. Cl. ..................................................... 536/127

(58) Field of Classification Search ........................ None
    See application file for complete search history.

(56) References Cited

U.S. PATENT DOCUMENTS

| | | |
|---|---|---|
| 4,343,934 A | 8/1982 | Jenner et al. |
| 4,380,476 A | 4/1983 | Mufti et al. |
| 4,783,526 A | 11/1988 | O'Brien et al. |
| 4,977,254 A | 12/1990 | Homer et al. |
| 5,141,860 A | 8/1992 | Bornemann et al. |
| 5,298,611 A | 3/1994 | Navia et al. |
| 5,498,709 A | 3/1996 | Navia et al. |
| 6,943,248 B2 | 9/2005 | Catani et al. |
| 2006/0188629 A1* | 8/2006 | Liesen et al. ................ 426/548 |

OTHER PUBLICATIONS

Vogel. Practical Organic Chemistry, Third Edition, Longman Group Limited 1956, pp. 122-139.*

* cited by examiner

*Primary Examiner*—Shaojia Anna Jiang
*Assistant Examiner*—Layla Bland
(74) *Attorney, Agent, or Firm*—Occhiuti Rohlicek & Tsao LLP

(57) ABSTRACT

The present application discloses a method for crystallizing sucralose, which comprises using a mixed solvent, which comprises two solvents with different boiling points, wherein the solvent with lower boiling point has higher solubility to sucralose than the solvent with higher boiling point. The method of the present invention has the advantages of low cost, high yield, mild processing conditions, stable quality, simple apparatuses and so on.

16 Claims, No Drawings

METHOD FOR CRYSTALLIZING SUCRALOSE

CROSS-REFERENCE TO RELATED APPLICATIONS

This application is being filed as a U.S. Utility application which claims the benefit of Chinese Patent Application No. 200610156768.3, filed on Dec. 27, 2006, the contents of which is hereby incorporated by reference in its entirety.

FIELD OF THE INVENTION

The present invention relates to a method for crystallizing sucralose.

BACKGROUND OF THE INVENTION

As a novel sweetener, sucralose is derived from sucrose by replacing the hydroxyls in the 4, 1' and 6' positions with chlorine. Its sweetness is 600 times of sucrose. Sucralose does not take part in human metabolism, thus has high safety and high resistance to acid hydrolysis. These advantages allow it being the most favorable highly effective sweetener, and are approved by more than thirty countries for use already. Patents of U.S. Pat. No. 4,343,934, U.S. Pat. No. 5,141,860, U.S. Pat. No. 4,977,254, U.S. Pat. No. 4,783,526, U.S. Pat. No. 4,380,476, U.S. Pat. No. 5,298,611 and so on illustrate a method for crystallizing sucralose, which use water as solvent for crystallization. The disadvantages of the method comprise: crystallization time is too long, which usually need several day; crystallization is incomplete, thus the crystallization mother liquor generally contains a large amount of sucralose, and the recovery of the mother liquor is relatively complicated; the product has relatively high moisture content, which adversely influences the stability of the product. U.S. Pat. No. 5,498,709 discloses a method for crystallizing sucralose, which uses ethyl acetate as the crystallization solvent. However, this method also has the problem of long crystallization time and low yield for the first operation. U.S. Pat. No. 6,943,248 provides a method for crystallizing sucralose, which uses a mixed solvent of methanol and ethyl acetate. However, owing to the too close boiling points of these solvents, it is difficult to separate out methanol and thereby obtain crystalline sucralose from ethyl acetate via simple distilling apparatuses. In this regard, U.S. Pat. No. 6,943,248 utilizes evaporating pipes to achieve the separation of methanol and ethyl acetate. However, the use of this apparatus is liable to leads to precipitation of sucralose in the pipeline, which renders further processes difficult to be continued. Consequently, it is obvious that this method is not suitable for industrial production.

SUMMARY OF THE INVENTION

Aiming at the shortages of the foregoing crystallization methods, the purpose of present invention is to provide a method for crystallizing sucralose, which uses more simple apparatus and provides crystalline sucralose of even better quality at higher yield.

In order to achieve the aforementioned purpose, the present invention provides a method for crystallizing sucralose, which comprises:

dissolving concentrate or solid that contains sucralose into a mixed solvent, which comprises two solvents with different boiling points, wherein the solvent with lower boiling point has higher solubility to sucralose than the solvent with higher boiling point;

stirring the mixture thus obtained to dissolve sucralose completely;

concentrating the solution thus obtained by distilling off the solvent under reduced pressure;

after the solvent with lower boiling point being distilled off, cooling the solution and allowing it to stand and crystallize; and obtaining crystalline sucralose after filtrating and drying.

In the method of the present invention, the difference between the boiling points under normal pressure of the two solvents of the mixed solvent is preferably greater than about 30° C. In view of achieving the purpose of the present invention, the higher the boiling-point difference between the boiling points of these solvents, the better the effect achieved by the present invention.

In the method of the present invention, it is further preferred that the solvent with lower boiling point has a solubility of greater than about 0.2 g/ml to sucralose. Preferably the solvent with higher boiling point has a solubility of less than about 0.05 g/ml to sucralose.

Specifically, the solvent with lower boiling point useful in the mixed solvent may be selected from a group consisted of, for example methanol, ethanol, water and acetonitrile. The higher-boiling-point solvent useful in the mixed solvent may be selected from a group consisted of, for example propyl acetate, butyl acetate, pentyl acetate, isopentyl acetate, n-butanol, isobutanol, n-pentanol and sec.-amyl alcohol. However, one skilled in the art would understand that the useful lower-boiling-point solvents and higher-boiling-point solvents are not limited to the above mentioned solvents. Any solvent useful in the fields of food and/or pharmacy can be used here, so long as the difference of boiling points between the lower-boiling-point solvents and the higher-boiling-point solvents is large enough.

When used, said solvents may be previously mixed before addition, or can be added sequentially.

The volume ratio between the two solvents constituting the mixed solvent can be conveniently determined with respect to the specifically selected solvents. Generally, the volume ratio between the higher-boiling-point solvent and the solvent with lower boiling point is in the range of about 0.5 to about 6.

The temperature at which the solution is concentrated can range from about 20° C. to about 65° C. depending on different degrees of vacuum.

In general, the temperature for standing and crystallizing is set at between about −5° C. and about 25° C.

The inventive method for crystallizing sucralose is as follows:

The sucralose (in form of solution) obtained from reaction is concentrated to obtain a syrup. Mixed solvent is added into syrup. The mixture is stirred to dissolve sucralose completely (heat may supplied if necessary). The solvent with lower boiling point is distilled out under certain degree of vacuum. As more and more solvent with lower boiling point being distilled out for the solution, the solution becomes more and more saturated. With the distillation goes on, crystals appears in the solution. The distillation is continued until almost all the solvent with lower boiling point is distilled out, and then stop concentrating. The solution is cooled with stirring, allowed to stand for a certain period of time, filtrated and dried, so as to obtain a final product of sucralose, with a one-pass yield of greater than 70%.

Generally, the solvent used in the last step of deacetylation reaction during the production of sucralose is methanol and the like. If methanol is used as the solvent with lower boiling point in the present invention, it is not necessary to distill out the solvent contained in the reaction mixture deacetylation reaction before crystallization. Instead, a solvent with higher boiling point is added into the mixture when there is still methanol remained, and concentration is continued under reduced pressure.

When crude sucralose is used in crystallization, the crude sucralose may be firstly dissolved in the solvent with lower boiling point, and then the solvent with higher boiling point is added in, followed by concentration and crystallization.

Compared with the reported processes for the crystallization of sucralose, the present invention has the advantages of less crystallization time, simpler operation, higher yield, simpler apparatuses, lower cost and so on. Being a product from non-aqueous system, the crystalline sucralose obtained in the present invention also has the advantage of resistant to hydrolysis compared with those obtained from aqueous systems.

EMBODIMENT OF THE INVENTION

The present invention will be further illustrated by the following examples, which however will not limit the present invention.

Example 1

20 g of trichlorosucrose-6-ethyl ester (with a purity of 99.0%) was subjected to deacylation reaction, so as to obtain 100 ml sucralose solution in methanol. The solution was concentrated to 40 ml, and 80 ml of n-butanol was added, with the water bath temperature being maintained at about 40° C. Methanol was distilled out at a vacuum of about −0.095 mpa. And after standing for a period of time, crystalline sucralose precipitated from the solution. Concentration was kept on via distillation until no methanol was distilled out. The solution was cooled to 5° C., followed by standing for 5 hours, filtrated, and dried under vacuum to obtain 14.3 g of sucralose as the final product (with a purity of 99.1%).

Example 2

20 g of trichlorosucrose-6-ethyl ester (with a purity of 99.0%) was subjected to deacylation reaction, so as to obtain 100 ml sucralose solution in methanol. The solution was concentrated to obtain dry solid. The solid thus obtained was dissolved in 30 ml of acetonitrile, then 80 ml of amyl acetate was added into the solution thus obtained. After stirring the solution homogeneously, acetonitrile was distilled out at a vacuum of about −0.095 mpa. And after standing for a period of time, crystalline sucralose precipitated from the solution. Concentration was kept on via distillation until no acetonitrile was distilled out. The solution was cooled to 10° C., followed by standing for 5 hours, filtrated, and dried under vacuum to obtain 15.7 g of sucralose as the final product (with a purity of 98.9%).

Example 3

20 g of sucralose (with a purity of 99.1%) obtained from example 1 was dissolved in 50 ml of methanol, and 70 ml of isobutanol was added into the solution. After stirring the solution homogeneously, methanol was distilled out at a vacuum of about −0.095 mpa. And after standing for a period of time, crystalline sucralose precipitated from the solution. Concentration was kept on via distillation until no methanol was distilled out. The solution was cooled to 10° C., followed by standing for 5 hours, filtrated, and dried under vacuum to obtain 16.3 g of sucralose as the final product (with a purity of 99.5%).

Example 4

20 g of sucralose (with a purity of 99.1%) obtained from example 1 was dissolved in 50 ml of methanol, and 100 ml of butyl acetate was added into the solution. After stirring the solution homogeneously, methanol was distilled out at a intra-temperature of 25° C. and under a vacuum of about −0.095 mpa. And after standing for a period of time, crystalline sucralose precipitated from the solution. Concentration was kept on via distillation until no methanol was distilled out. The solution was cooled to 0° C., followed by standing for 5 hours, filtrated, and dried under vacuum to obtain 17.5 g of sucralose as the final product (with a purity of 99.3%).

Example 5

20 g of sucralose (with a purity of 98.9%) obtained from example 2 was dissolved in 60 ml of methanol, and 200 ml of amyl acetate was added into the solution. After stirring the solution homogeneously, ethanol was distilled out at an intra-temperature of 50° C. and under a vacuum of about −0.085 Mpa. And after standing for a period of time, crystalline sucralose precipitated from the solution. Concentration was kept on via distillation until no ethanol was distilled out. The solution was cooled to 20° C., followed by standing for 5 hours, filtrated, and dried under vacuum to obtain 17.2 g of sucralose as the final product (with a purity of 99.2%).

What is claimed is:

1. A method for crystallizing sucralose comprising:
    Dissolving a concentrate or a solid that contains sucralose into a mixed solvent, which comprises two solvents with different boiling points, wherein the solvent with a lower boiling point has a higher solubility to sucralose than the solvent with a higher boiling point;
    stirring the mixture thus obtained to dissolve sucralose completely;
    concentrating the solution thus obtained by distilling off the solvent under reduced pressure;
    after the solvent with a lower boiling point having been distilled off, cooling the solution and allowing it to stand and crystallize; and
    obtaining crystalline sucralose after filtrating and drying;
    wherein the solvent with a lower boiling point is selected from a group consisting of methanol and ethanol, and the solvent with a higher boiling point is selected from a group consisting of propyl acetate, butyl acetate, pentyl acetate, isopentyl acetate, n-butanol, isobutanol, n-pentanol, and secondary amyl alcohol.

2. The method according to claim 1, wherein the difference between the boiling points under normal pressure of the two solvents is greater than about 30° C.

3. The method according to claim 1, wherein the solvent with a lower boiling point has a solubility of greater than about 0.2 g/ml to sucralose.

4. The method according to claim 1, wherein the solvent with a higher boiling point has a solubility of less than about 0.05 g/ml to sucralose.

5. The method according to claim 1, wherein said two solvents are premixed before addition.

6. The method according to claim 1, wherein the volume ratio between the solvent with a higher boiling point and the solvent with a lower boiling point is in the range of from about 0.5 to about 6.

7. The method according to claim 1, wherein the temperature at which the solution is concentrated ranges from about 20° C. to about 65° C.

8. The method according to claim 1, wherein the temperature for standing and crystallizing is set at between about −5° C. and about 25° C.

9. The method according to claim 2, wherein the solvent with a lower boiling point has a solubility of greater than about 0.2 g/ml to sucralose.

10. The method according to claim 2, wherein the solvent with a higher boiling point has a solubility of less than about 0.05 g/ml to sucralose.

11. The method according to claim 2, wherein said two solvents are premixed before addition.

12. The method according to claim 2, wherein the volume ratio between the solvent with a higher boiling point and the solvent with a lower boiling point is in the range of from about 0.5 to about 6.

13. The method according to claim 2, wherein the temperature at which the solution is concentrated can range ranges from about 20° C. to about 65° C.

14. The method according to claim 2, wherein the temperature for standing and crystallizing is set at between about −5° C. and about 25° C.

15. The method of claim 1, wherein the two solvents are added sequentially.

16. The method of claim 2, wherein the two solvents are added sequentially.

* * * * *